US008058486B2

(12) United States Patent
Merkel et al.

(10) Patent No.: US 8,058,486 B2
(45) Date of Patent: *Nov. 15, 2011

(54) INTEGRATED PROCESS TO PRODUCE 2,3,3,3-TETRAFLUOROPROPENE

(75) Inventors: Daniel C. Merkel, West Seneca, NY (US); Hsueh Sung Tung, Getzville, NY (US); Konstantin A. Pokrovski, Orchard Park, NY (US); Selma Bektesevic, Williamsville, NY (US); Robert C. Johnson, Lancaster, NY (US); Haiyou Wang, Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 198 days.

This patent is subject to a terminal disclaimer.

(21) Appl. No.: 12/404,130

(22) Filed: Mar. 13, 2009

(65) Prior Publication Data

US 2011/0207975 A9    Aug. 25, 2011

Related U.S. Application Data

(63) Continuation-in-part of application No. 11/619,592, filed on Jan. 3, 2007.

(60) Provisional application No. 61/038,327, filed on Mar. 20, 2008.

(51) Int. Cl.
*C07C 17/25* (2006.01)

(52) U.S. Cl. ........ 570/155; 570/135; 570/167; 570/164; 570/179; 570/188

(58) Field of Classification Search ........................ None
See application file for complete search history.

(56) References Cited

U.S. PATENT DOCUMENTS

| 2,931,840 | A | 4/1960 | Marquis |
| 4,900,874 | A | 2/1990 | Ihara et al. |
| 5,162,594 | A | 11/1992 | Krespan |
| 2007/0197842 | A1* | 8/2007 | Mukhopadhyay et al. ... 570/155 |

FOREIGN PATENT DOCUMENTS

| WO | WO2007079431 | 7/2007 |
| WO | WO2009125199 | 10/2009 |

OTHER PUBLICATIONS

Banks et al., Journal of Fluorine Chemistry, vol. 82, Issue 2, pp. 171-174 (1997). US.

* cited by examiner

*Primary Examiner* — Sudhakar Katakam
(74) *Attorney, Agent, or Firm* — Bruce Bradford

(57) ABSTRACT

A method for preparing 2,3,3,3-tetrafluoroprop-1-ene comprising (a) providing a starting composition comprising at least one compound having a structure selected from Formulae I, II and III:

$$CX_2=CCl-CH_2X \quad \text{(Formula I)}$$

$$CX_3-CCl=CH_2 \quad \text{(Formula II)}$$

$$CX_3-CHCl-CH_2X \quad \text{(Formula III)}$$

wherein X is independently selected from F, Cl, Br, and I, provided that at least one X is not fluorine;
(b) contacting said starting composition with a first fluorinating agent to produce a first intermediate composition comprising 2-chloro-3,3,3-trifluoropropene and a first chlorine-containing byproduct; (c) contacting said first intermediate composition with a second fluorinating agent to produce a second intermediate composition comprising 2-chloro-1,1,1,2-tetrafluoropropane and a second chlorine-containing byproduct; and (d) catalytically dehydrochlorinating at least a portion of said 2-chloro-1,1,1,2-tetrafluoropropane to produce a reaction product comprising 2,3,3,3-tetrafluoroprop-1-ene.

19 Claims, 9 Drawing Sheets

FIRST STEP (OPTION A) OF AN INTEGRATED 3-STEP PROCESS
FOR MANUFACTURE OF 1234yf STARTING WITH
1,1,2,3-TETRACHLOROPROPENE (TCP) OR 1,1,1,2,3-PENTACHLOROPROPANE (240db)

------ MEANS OPTIONAL EQUIPMENT/ASSOCIATED PROCESS LINES
——— HIGHLIGHTS DESIGN OPTIONS

FIRST STEP (OPTION B) OF AN INTEGRATED 3-STEP PROCESS FOR MANUFACTURE OF 1234yf STARTING WITH 1,1,2,3-TETRACHLOROPROPENE (TCP) OR 1,1,1,2,3-PENTACHLOROPROPANE (240db)

FIRST STEP (OPTION C) OF AN INTEGRATED 3-STEP PROCESS FOR MANUFACTURE OF 1234yf STARTING WITH 1,1,2,3-TETRACHLOROPROPENE (TCP) OR 1,1,1,2,3-PENTACHLOROPROPANE (240db)

SECOND STEP (OPTION A) OF AN INTEGRATED 3-STEP PROCESS
FOR MANUFACTURE OF 1234yf STARTING WITH
1,1,2,3-TETRACHLOROPROPENE (TCP) OR 1,1,1,2,3-PENTACHLOROPROPANE (240db)

SECOND STEP (OPTION B) OF AN INTEGRATED 3-STEP PROCESS FOR MANUFACTURE OF 1234yf STARTING WITH 1,1,2,3-TETRACHLOROPROPENE (TCP) OR 1,1,1,2,3-PENTACHLOROPROPANE (240db)

THIRD STEP (OPTION A) OF AN INTEGRATED 3-STEP PROCESS FOR MANUFACTURE OF 1234yf STARTING WITH 1,1,2,3-TETRACHLOROPROPENE (TCP) OR 1,1,1,2,3-PENTACHLOROPROPANE (240db)

THIRD STEP (OPTION B) OF AN INTEGRATED 3-STEP PROCESS FOR MANUFACTURE OF 1234yf STARTING WITH 1,1,2,3-TETRACHLOROPROPENE (TCP) OR 1,1,1,2,3-PENTACHLOROPROPANE (240db)

INTEGRATED PROCESS TO PRODUCE 2,3,3,3-TETRAFLUOROPROPENE

RELATED APPLICATIONS

The present application is related to and claims the priority benefit of U.S. Provisional Patent Application No. 61/038,327, which was filed on Mar. 20, 2008. The present application is also a continuation-in-part of U.S. patent application Ser. No. 11/619,592, filed Jan. 3, 2007.

BACKGROUND OF INVENTION (1) Field of Invention

This invention relates to novel methods for preparing fluorinated organic compounds, and more particularly to methods of producing fluorinated olefins.

(2) Description of Related Art

Hydrofluoroolefins (HFOs), such as tetrafluoropropenes (including 2,3,3,3-tetrafluoroprop-1-ene (HFO-1234yf)), are known to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFOs do not contain chlorine and, thus, pose no threat to the ozone layer. In addition, HFO-1234yf is a low global warming compound with low toxicity and hence can meet increasingly stringent requirements for refrigerants in mobile air conditioning.

Several methods of preparing HFOs are known. For example, U.S. Pat. No. 4,900,874 (Ihara et al) describes a method of making fluorine containing olefins by contacting hydrogen gas with fluorinated alcohols. Although this appears to be a relatively high-yield process, commercial scale handling of hydrogen gas at high temperature is hazardous. Also, the cost of commercially producing hydrogen gas, such as building an on-site hydrogen plant, is economically costly.

U.S. Pat. No. 2,931,840 (Marquis) describes a method of making fluorine containing olefins by pyrolysis of methyl chloride and tetrafluoroethylene or chlorodifluoromethane. This process is a relatively low yield process and a very large percentage of the organic starting material is converted to unwanted and/or unimportant byproducts, including a sizeable amount of carbon black which tends to deactivate the catalyst used in the process.

The preparation of HFO-1234yf from trifluoroacetylacetone and sulfur tetrafluoride has been described (See Banks, et al., *Journal of Fluorine Chemistry*, Vol. 82, Iss. 2, p. 171-174 (1997)). Also, U.S. Pat. No. 5,162,594 (Krespan) discloses a process wherein tetrafluoroethylene is reacted with another fluorinated ethylene in the liquid phase to produce a polyfluoroolefin product.

However, there remains a need for an economic means of producing hydrofluoroolefins, such as HFO-1234yf. The present invention satisfies this need among others.

SUMMARY OF THE INVENTION

Applicants have found a method for producing fluorinated organic compounds, including hydrofluoropropenes, such as HFO-1234yf. In one aspect, the present invention involves an integrated manufacturing process to produce 2,3,3,3-tetrafluoropropene from a chlorinated hydrocarbon or chlorinated olefin. Preferably, the integrated manufacturing process includes three separate reaction steps which are each optionally followed by one or more purification processes. The present invention is advantageous over other known processes for producing HFO-1234yf in that the process includes the ability to recycle unreacted starting materials to maximize raw material utilization and product yields. It also is characterized by the ability to isolate by-products that are commercially valuable.

Accordingly, provided is a method for preparing 2,3,3,3-tetrafluoroprop-1-ene comprising: (a) providing a starting composition comprising at least one compound having a structure selected from Formula I, II and III:

$CX_2=CCl-CH_2X$ (Formula I)

$CX_3-CCl=CH_2$ (Formula II)

$CX_3-CHCl-CH_2X$ (Formula III)

wherein X is independently selected from Cl, Br, and I; (b) contacting said starting composition with a first fluorinating agent to produce a first intermediate composition comprising 2-chloro-3,3,3-trifluoropropene and a first chlorine-containing byproduct; (c) contacting said first intermediate composition with a second fluorinating agent to produce a second intermediate composition comprising 2-chloro-1,1,1,2-tetrafluoropropane; and (d) catalytically dehydrochlorinating at least a portion of said 2-chloro-1,1,1,2-tetrafluoropropane to produce a reaction product comprising 2,3,3,3-tetrafluoroprop-1-ene and a second chlorine-containing byproduct.

DETAILED DESCRIPTION OF PREFERRED EMBODIMENTS OF THE INVENTION

Figure 1:
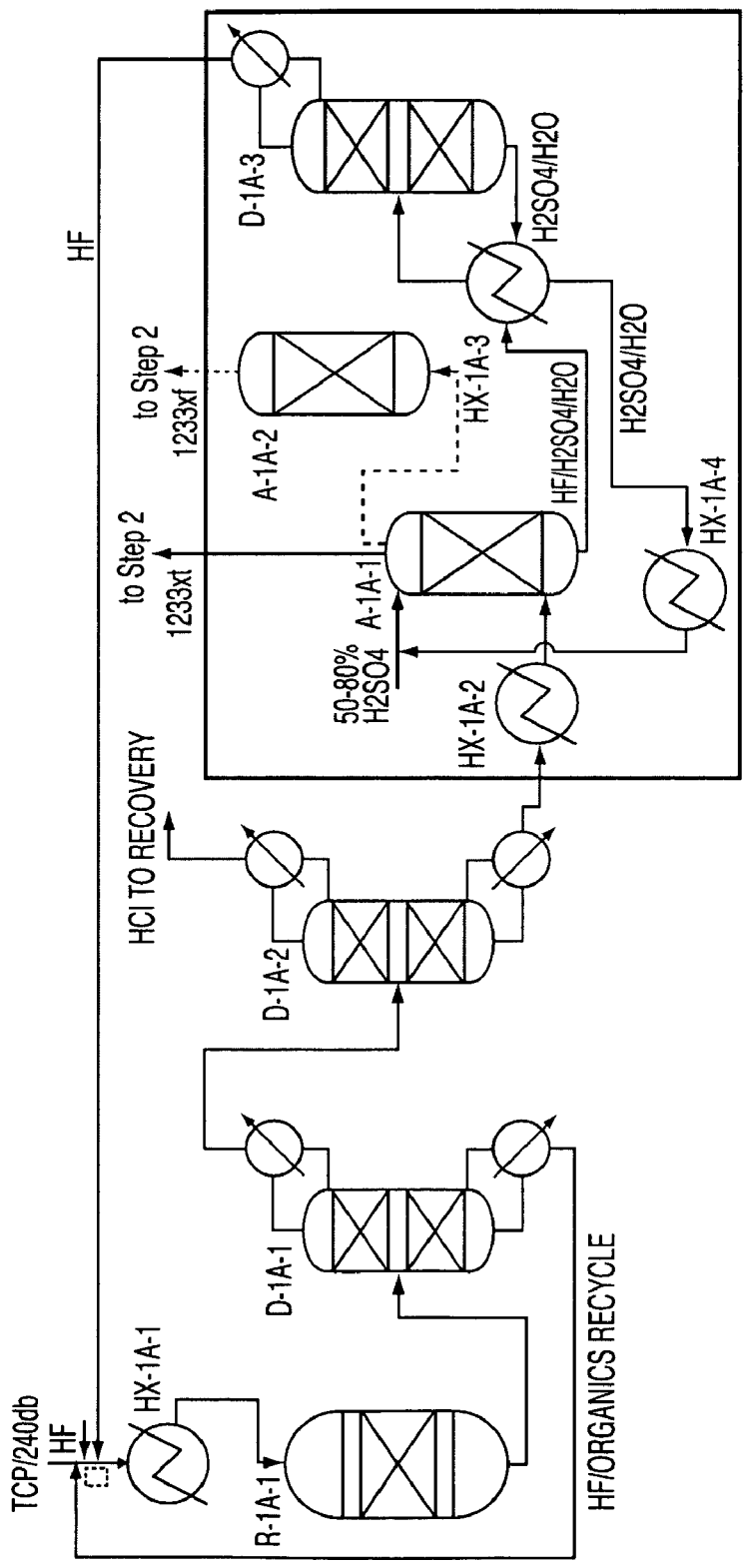
FIG. 1 is a flow diagram showing a first preferred embodiment of a first step of an integrated 3-step process for producing HFO-1234yf starting from 1,1,2,3-tetrachloropropene or 1,1,1,2,3-pentachloropropane.

According to a preferred embodiment, the present invention comprises an integrated manufacturing process for making 2,3,3,3-tetrafluoroprop-1-ene. The preferred starting material is one or more chlorinated compounds according to Formulae I, II and/or III:

$$CX_2=CCl-CH_2X \quad \text{(Formula I)}$$

$$CX_3-CCl=CH_2 \quad \text{(Formula II)}$$

$$CX_3-CHCl-CH_2X \quad \text{(Formula III)}$$

wherein X is independently selected from F, Cl, Br, and I, provided that at least one X is not fluorine;

Preferably, these compounds contain at least one chlorine, more preferably a majority of X is chlorine, and even more preferably all X is chlorine.

Preferably, the method generally comprises at least three reaction steps. In the first step, a starting composition, preferably comprising 1,1,2,3-tetrachloropropene (TCP) and/or 1,1,1,2,3-pentachloropropane (HCC-240db), reacts with anhydrous HF in a first vapor phase reactor (fluorination reactor) to produce a mixture of HCFO-1233xf (2-chloro-3,3,3-trifluoropropene) and HCl. Preferably the reaction occurs in the presence of a catalyst, such as a fluorinated chromium oxide. The reaction is conducted in a first vapor phase reactor, preferably at a reaction temperature of about 200-400° C. and a reaction pressure of about 0-200 psig. The effluent stream exiting the vapor phase reactor may optionally comprise additional components, such as un-reacted HF, heavy intermediates, and HFC-245cb.

This reaction may be conducted in any reactor suitable for a vapor phase fluorination reaction. Preferably the reactor is constructed from materials which are resistant to the corrosive effects of hydrogen fluoride and catalyst such as Hastalloy, Inconel, Monel. In case of a vapor phase process, the reactor is filled with a vapor phase fluorination catalyst. Any fluorination catalysts known in the art may be used in this process. Suitable catalysts include, but are not limited to chromium, aluminum, cobalt, manganese, nickel and iron oxides, hydroxides, halides, oxyhalides, inorganic salts thereof and their mixtures. Combinations of catalysts suitable for the present invention nonexclusively include $Cr_2O_3$, $FeCl_3/C$, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Chromium oxide/aluminum oxide catalysts are described in U.S. Pat. No. 5,155,082 which is incorporated herein by reference. Chromium (III) oxides such as crystalline chromium oxide or amorphous chromium oxide are preferred with amorphous chromium oxide being most preferred. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to drive the reaction.

In the second step, the HCFO-1233xf is converted to HCFC-244bb in a liquid phase reactor, preferably TFE or PFA-lined. Preferably, the process is performed at about 70-120° C. and about 50-120 psig.

Any liquid phase fluorination catalyst may be used in the invention. A non-exhaustive list include Lewis acids, transition metal halides, transition metal oxides, Group IVb metal halides, a Group Vb metal halides, or combinations thereof. Non-exclusive examples of liquid phase fluorination catalysts are an antimony halide, a tin halide, a tantalum halide, a titanium halide, a niobium halide, and molybdenum halide, an iron halide, a fluorinated chrome halide, a fluorinated chrome oxide or combinations thereof. Specific non-exclusive examples of liquid phase fluorination catalysts are $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof. Antimony pentachloride is most preferred.

These catalysts can be readily regenerated by any means known in the art if they become deactivated. One suitable method of regenerating the catalyst involves flowing a stream of chlorine through the catalyst. For example, from about 0.002 to about 0.2 lb per hour of chlorine can be added to the liquid phase reaction for every pound of liquid phase fluorination catalyst. This may be done, for example, for from about 1 to about 2 hours or continuously at a temperature of from about 65° C. to about 100° C.

In the third step, the HCFC-244bb is fed to a second vapor phase reactor (dehydrochlorination reactor) to be dehydrochlorinated to make the desired product HFO-1234yf (2,3,3,3-tetrafluoroprop-1-ene). This reactor contains a catalyst that can catalytically dehydrochlorinate HCFC-244bb to make HFO-1234yf.

The catalysts may be metal halides, halogenated metal oxides, neutral (or zero oxidation state) metal or metal alloy, or activated carbon in bulk or supported form. When metal halides or metal oxides catalysts are used, preferably mono-, bi-, and tri-valent metal halides, oxide and their mixtures/combinations, and more preferably mono-, and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source.

When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, and Inconel 625.

Preferred catalysts include activated carbon, stainless steel (e.g. SS 316), austenitic nickel-based alloys (e.g. Inconel 625), nickel, fluorinated 10% CsCl/MgO, and 10% CsCl/$MgF_2$. The reaction temperature is preferably about 300-550° C. and the reaction pressure is preferably about 0-150 psig. Preferably, the reactor effluent is fed to a caustic scrubber or to a distillation column to remove the by-product of HCl to produce an acid-free organic product which, optionally, may undergo further purification.

The general reaction path is provided below:

Step 1A:

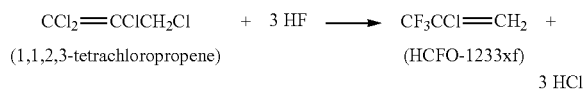

(1,1,2,3-tetrachloropropene)      (HCFO-1233xf)

3 HCl

-continued

Step 1B:

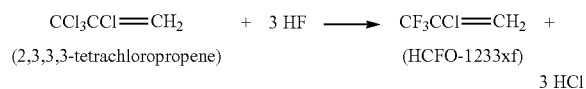

(2,3,3,3-tetrachloropropene) (HCFO-1233xf)
3 HCl

Step 1C:

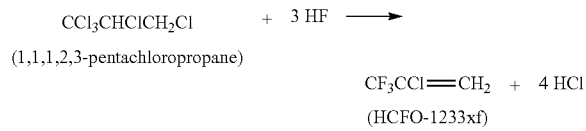

(1,1,1,2,3-pentachloropropane)

$CF_3CCl={=}CH_2$ + 4 HCl (HCFO-1233xf)

Step 2:

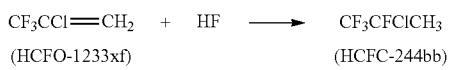

(HCFO-1233xf) (HCFC-244bb)

Step 3:

(HCFC-244bb) (HFO-1234yf)

In addition to these three general steps, preferred embodiments comprise one or more of the following steps:

Recycle of Unreacted HF and Intermediates:

Subsequent to Step (1) above, the effluent stream exiting the vapor phase reactor is fed to a first recycle column. The majority of the un-reacted HF and heavy intermediates are separated from the bottom of the first recycle column and fed back to the vapor phase reactor. The lighter components, including HCl, HCFO-1233xf, HCFC-244bb, HFC-245cb, and small amounts of HF are fed to next unit operation as a crude first intermediate stream.

Removal of HCl:

The HCl in the crude intermediate stream is removed using an HCl column. High purity HCl is isolated from the top of the column and absorbed in de-ionized water as concentrated HCl which, optionally, can be recovered for sale. The remaining components exit the bottom of the HCl column and are fed as a purified first intermediate stream into the liquid phase reactor of Step (2).

Recycle of Excess HF:

Subsequent to Step (2) above, a crude second intermediate stream comprising the HCFC-244bb and HF as a reaction byproduct exits the liquid phase reactor and is fed to a second recycle column to isolate the excess HF as the bottom effluent of the column and recycle the bottoms back to the liquid phase reactor. The overhead contains mainly the HCFC-244bb and HF. The overhead stream is fed to the next unit operation.

Sulfuric Acid Extraction or Phase Separation for HF Recovery/Recycle:

The overhead stream from the liquid phase recycle column that contains crude product mixture of HCFC-244bb and about 30 wt % HF is fed to a sulfuric acid extractor or a phase separator for removal of HF from this mixture. HF is either dissolved in the sulfuric acid or phase separated from the organic mixture. HF is desorbed from the sulfuric acid/HF mixture by heating and distillation and recycled back to the reactor. In case a phase separator is used, HF is phase-separated and recycled back to the reactor. The organic mixture either from the overhead of the sulfuric acid extractor or from the bottom layer of the phase separator is fed to the dehydrochlorination reactor of Step (3).

Purification of Final Product:

The acid-free organic product produced in Step (3) is fed to one or more, preferably two, distillation columns for purification of final product. The first column is used to remove the lighter components and the second column is used to purify the final product, HFO-1234yf. The un-reacted HCFC-244bb and HCFO-1233xf are isolated from the bottom of the second distillation column and recycled back to the second step (hydrofluorination of HCFO-1233xf).

Referring to FIG. 1, shown is a preferred embodiment of operations 1 through 3. Here, TCP (or HCC-240db) and excess HF are simultaneously fed to a vaporizer HX-1A-1 and then into a vapor phase reactor R-1A-1. The reaction temperature is about 200-400° C. and the reaction pressure is about 0-200 psig. The catalyst in R-1A-1 is fluorinated chromium oxide. The reactor effluent comprising unreacted TCP (or HCC-240db), partially fluorinated intermediates and by-products, overfluorinated by-products, HF, HCFO-1233xf, and HCl, then enters recycle column D-1A-1 where a stream comprising mainly unreacted TCP (or HCC-240db), partially fluorinated intermediates, and the majority of the HF exits the bottom of the recycle column and is recycled back to the Step 1 reactor R-1A-1 via vaporizer HX-1A-1. A stream consisting of mainly HCFO-1233xf, HF, and HCl exits the top of the recycle column and enters HCl column D-1A-2. A stream consisting of mainly HCl by-product exits the top of the HCl column and is fed to an HCl recovery system. The recovered HCl by-product can be sold for profit. The HCl column bottoms consisting mainly of HCFO-1233xf and HF are then fed into an HF recovery system. The HF recovery system starts with the HCFO-1233xf/HF stream being vaporized in heat exchanger HX-1A-2 and fed into HF absorption column A-1A-1. Here a liquid stream of 50-80% $H_2SO_4$ contacts the gaseous HCFO-1233xf/HF stream and absorbs the majority of the HF. The stream exiting the bottom of A-1A-1 consists of $HF/H_2SO_4/H_2O$ and is fed to heat exchanger HX-1A-3 where it is heated to a temperature sufficient to flash the majority of the HF along with small amounts of $H_2O$ and $H_2SO_4$. This stream is fed to HF recovery distillation column D-1A-3. The liquid remaining after the HF is flashed off in HX-1A-3 consisting mainly of $H_2SO_4$ and $H_2O$ (with 0-4% HF) is cooled in HX-1A-4 and recycled back to HF absorption column A-1A-1. The HF recovery column, D-1A-3, bottoms stream consisting of mainly $H_2SO_4$ and $H_2O$ are recycled back to heat exchanger HX-1A-3. Anhydrous HF is recovered from the top of the HF recovery column, D-1A-3, and is recycled back to the Step 1 reactor R-1A-1 via vaporizer HX-1A-1. The stream exiting the top of HF absorption column A-1A-1 consisting of mainly HCFO-1233xf (trace HF) is sent forward to Step 2. Optionally, before being sent forward to step 2, the stream is fed to a polishing system A-1A-2 where the gaseous stream contacts a water or a caustic solution to remove trace HF and is subsequently dried with a desiccant. After deactivation of the catalyst in reactor R-1A-1 it can be regenerated in-situ by heating to 300-400° C. and passing an oxidizing agent such as $O_2$ or $Cl_2$ over it for a prescribed period of time.

Figure 2:
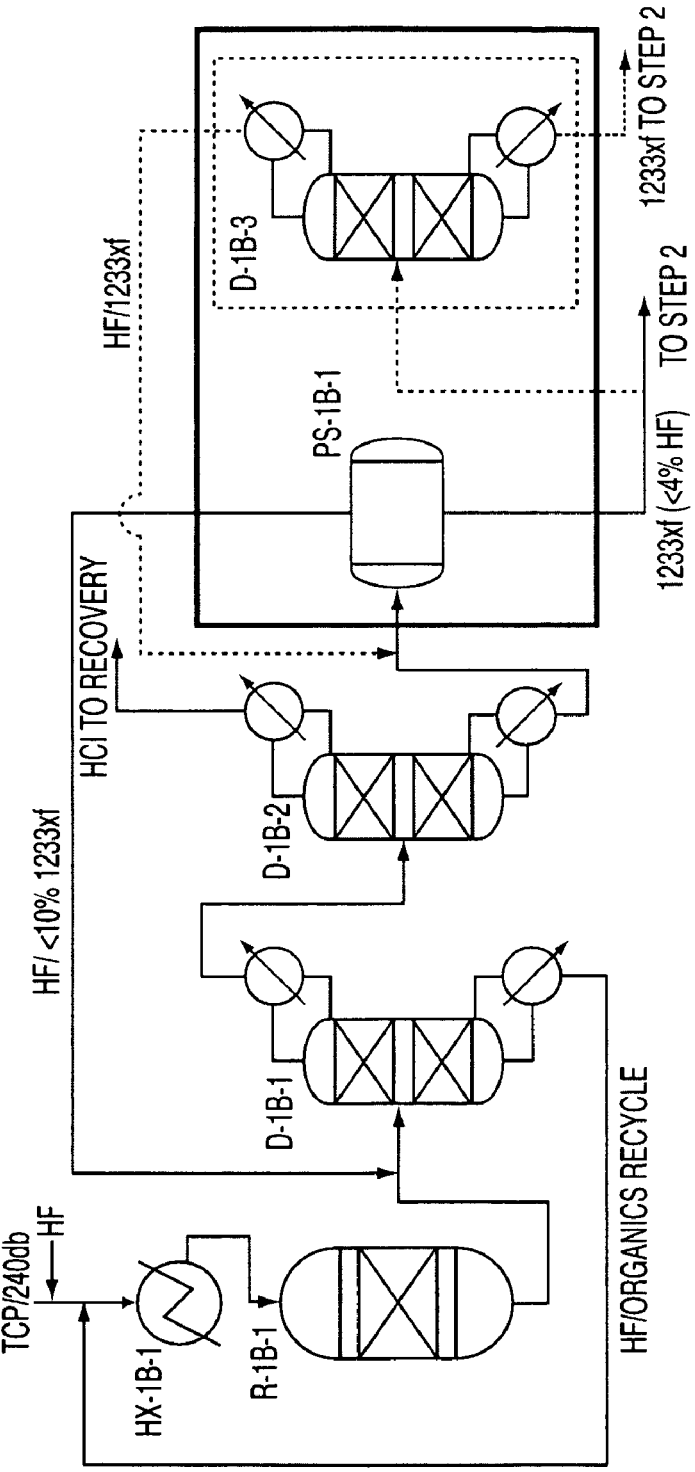
FIG. 2 is a flow diagram showing a second preferred embodiment of a first step of an integrated 3-step process for producing HFO-1234yf starting from 1,1,2,3-tetrachloropropene or 1,1,1,2,3-pentachloropropane.

Referring to FIG. 2, shown is another preferred embodiment of operations 1 through 3. Here, TCP (or HCC-240db) and excess HF are simultaneously fed to a vaporizer HX-1B-1 and then into a vapor phase reactor R-1B-1. The reaction temperature is about 200-400° C. and the reaction pressure is about 0-200 psig. The catalyst in R-1B-1 is fluorinated chromium oxide. The reactor effluent consisting of unreacted TCP (or HCC-240db), partially fluorinated intermediates and by-products, overfluorinated by-products, HF, HCFO-1233xf, and HCl, then enters recycle column D-1B-1 where a stream consisting of mainly unreacted TCP (or HCC-240db), partially fluorinated intermediates, and the majority of the HF exits the bottom of the recycle column and is recycled back to the Step 1 reactor R-1B-1 via vaporizer HX-1B-1. A stream consisting of mainly HCFO-1233xf, HF, and HCl exits the top of the recycle column and enters HCl column D-1B-2. A stream consisting of mainly HCl by-product exits the top of the HCl column and is fed to an HCl recovery system. The recovered HCl by-product can be sold for profit. The HCl column bottoms consisting mainly of HCFO-1233xf and HF are then fed into an HF recovery system. The HF recovery system starts with the HCFO-1233xf/HF stream being fed into phase separation system PS-1B-1. Here the stream is cooled to −40-0° C. The HF rich top layer (<10% HCFO-1233xf) is recycled back to the recycle column D-1B-1. The organic rich bottom layer containing mainly HCFO-1233xf (<4% HF) is sent forward to Step 2. Optionally, before being sent forward to Step 2, the stream is fed to a distillation column D-1B-3. A stream consisting of mainly HCFO-1233xf/HF azeotrope exits the top of the column and is recycled back to the Step 1 phase separator, PS-1B-1. The column bottoms consisting mainly of HCFO-1233xf are sent forward to Step 2. After deactivation of the catalyst in reactor R-1B-1 it can be regenerated in-situ by heating to 300-400° C. and passing an oxidizing agent such as $O_2$ or $Cl_2$ over it for a prescribed period of time.

Figure 3:
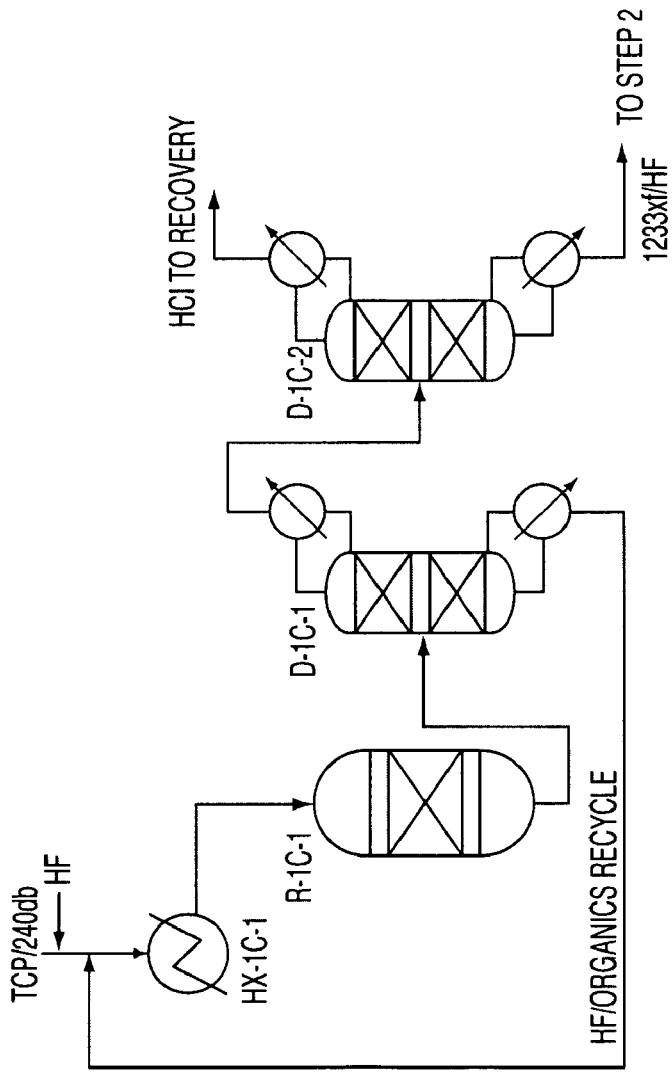
FIG. 3 is a flow diagram showing a third preferred embodiment of a first step of an integrated 3-step process for producing HFO-1234yf starting from 1,1,2,3-tetrachloropropene or 1,1,1,2,3-pentachloropropane.

Referring to FIG. 3, shown is another preferred embodiment of operations 1 through 3. Here, TCP (or HCC-240db) and excess HF are simultaneously fed to a vaporizer HX-1C-1 and then into a vapor phase reactor R-1C-1. The reaction temperature is about 200-400° C. and the reaction pressure is about 0-200 psig. The catalyst in R-1C-1 is fluorinated chromium oxide. The reactor effluent consisting of unreacted TCP (or HCC-240db), partially fluorinated intermediates and by-products, overfluorinated by-products, HF, HCFO-1233xf, and HCl, then enters recycle column D-1C-1 where a stream consisting of mainly unreacted TCP (or HCC-240db), partially fluorinated intermediates, and the majority of the HF exits the bottom of the recycle column and is recycled back to the Step 1 reactor R-1C-1 via vaporizer HX-1C-1. A stream consisting of mainly HCFO-1233xf, HF, and HCl exits the top of the recycle column and enters HCl column D-1C-2. A stream consisting of mainly HCl by-product exits the top of the HCl column and is fed to an HCl recovery system. The recovered HCl by-product can be sold for profit. The HCl column bottoms consisting mainly of HCFO-1233xf and HF are then sent forward to Step 2 without removal of HF. After deactivation of the catalyst in reactor R-1C-1 it can be regenerated in-situ by heating to 300-400° C. and passing an oxidizing agent such as $O_2$ or $Cl_2$ over it for a prescribed period of time.

Figure 4:
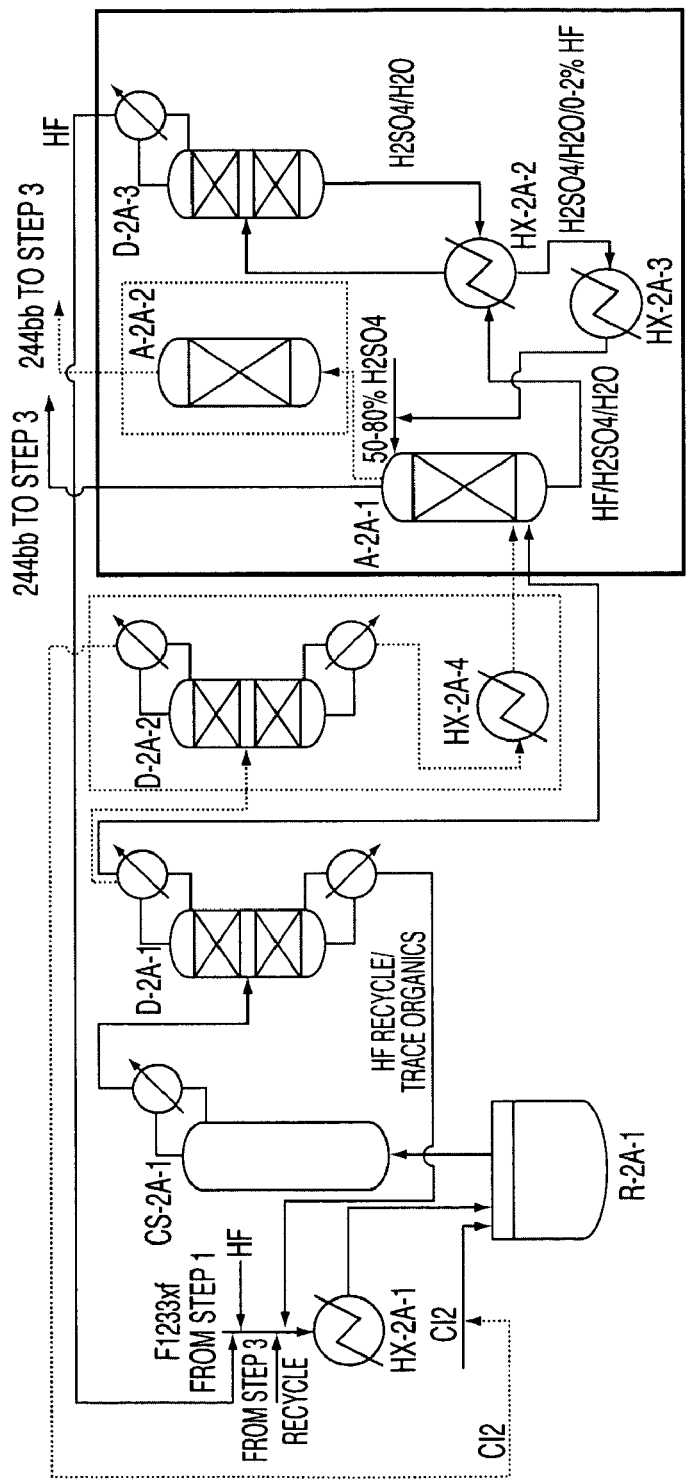
FIG. 4 is a flow diagram showing a first preferred embodiment of a second step of an integrated 3-step process for producing HFO-1234yf starting from 1,1,2,3-tetrachloropropene or 1,1,1,2,3-pentachloropropane.

Referring to FIG. 4, shown is a preferred embodiment of operations 4 through 6. Here, the HCFO-1233xf containing stream from Step 1, Options A, B, or C and excess HF are simultaneously fed to a vaporizer HX-2A-1 and then into a liquid phase reactor R-2A-1. R-2A-1 is a TFE or PFA-lined liquid phase reactor, run at 70-120° C. and 50-120 psig. The catalyst in R-2A-1 is $SbCl_5$ or other Lewis acid catalyst. A catalyst stripper column CS-2A-1 is connected to the reactor, R-2A-1, and serves the purpose of knocking down and returning entrained catalyst, some HF, and some unreacted HCFO-1233xf back to the reactor for further reaction. $Cl_2$ may also be fed to the reactor to keep the catalyst active. It may be fed continuously or batchwise as needed. The stream exiting the top of catalyst stripper CS-2A-1 consisting mainly of HCFC-244bb and HF (plus small amounts of unreacted HCFO-1233xf and $Cl_2$ may also be present) is fed to a recycle column D-2A-1 where a stream consisting of mainly HF (trace organic) exits the bottom of the recycle column and is recycled back to the Step 2 reactor R-2A-1 via vaporizer HX-2A-1. A stream consisting of mainly HCFC-244bb and HF (plus small amounts of unreacted HCFO-1233xf and $Cl_2$ may also be present) exits the top of the recycle column and is then fed into an HF recovery system. The HF recovery system starts with the gaseous HCFC-244bb and HF (plus small amounts of unreacted HCFO-1233xf and $Cl_2$ may also be present) stream being fed into HF absorption column A-2A-1. Here a liquid stream of 50-80% $H_2SO_4$ contacts the gaseous HCFC-244bb/HF stream and absorbs the majority of the HF. The stream exiting the bottom of A-2A-1 consists of $HF/H_2SO_4/H_2O$ and is fed to heat exchanger HX-2A-2 where it is heated to a temperature sufficient to flash the majority of the HF along with small amounts of $H_2O$ and $H_2SO_4$. This stream is fed to HF recovery distillation column D-2A-3. The liquid remaining after the HF is flashed off in HX-2A-2 consisting mainly of $H_2SO_4$ and $H_2O$ (with 0-4% HF) is cooled in HX-2A-3 and recycled back to HF absorption column A-2A-1. The HF recovery column, D-2A-3, bottoms stream consisting of mainly $H_2SO_4$ and $H_2O$ are recycled back to heat exchanger HX-2A-2. Anhydrous HF is recovered from the top of the HF recovery column, D-2A-3, and is recycled back to the Step 2 reactor R-2A-1 via vaporizer HX-2A-1. The stream exiting the top of HF absorption column A-2A-1 consisting of mainly HCFC-244bb (plus small amounts of unreacted HCFO-1233xf and $Cl_2$ may also be present) is sent forward to Step 3. Optionally, before being sent forward to Step 3, the stream is fed to a polishing system A-2A-2 where the gaseous stream contacts a water or a caustic solution (and bisulfite as needed to destroy any $Cl_2$) to remove trace HF and is subsequently dried with a desiccant.

Another option is to add a $Cl_2$ recovery distillation column, D-2A-2 and heat exchanger HX-2A-4 after the recycle column D-2A-1 and before HF recovery. The stream exiting the top of the recycle column is fed into the $Cl_2$ recovery column and $Cl_2$ is taken overhead and recycled back to the Step 2 reactor, R-2A-1. The $Cl_2$ recovery column bottom stream consisting of mainly HCFC-244bb and HF (plus small amount of unreacted HCFO-1233xf) is vaporized in heat exchanger HX-2A-4 and fed to the HF recovery system described above. This eliminates the need for bisulfite in the optional HCFC-244bb polishing system.

Figure 5:
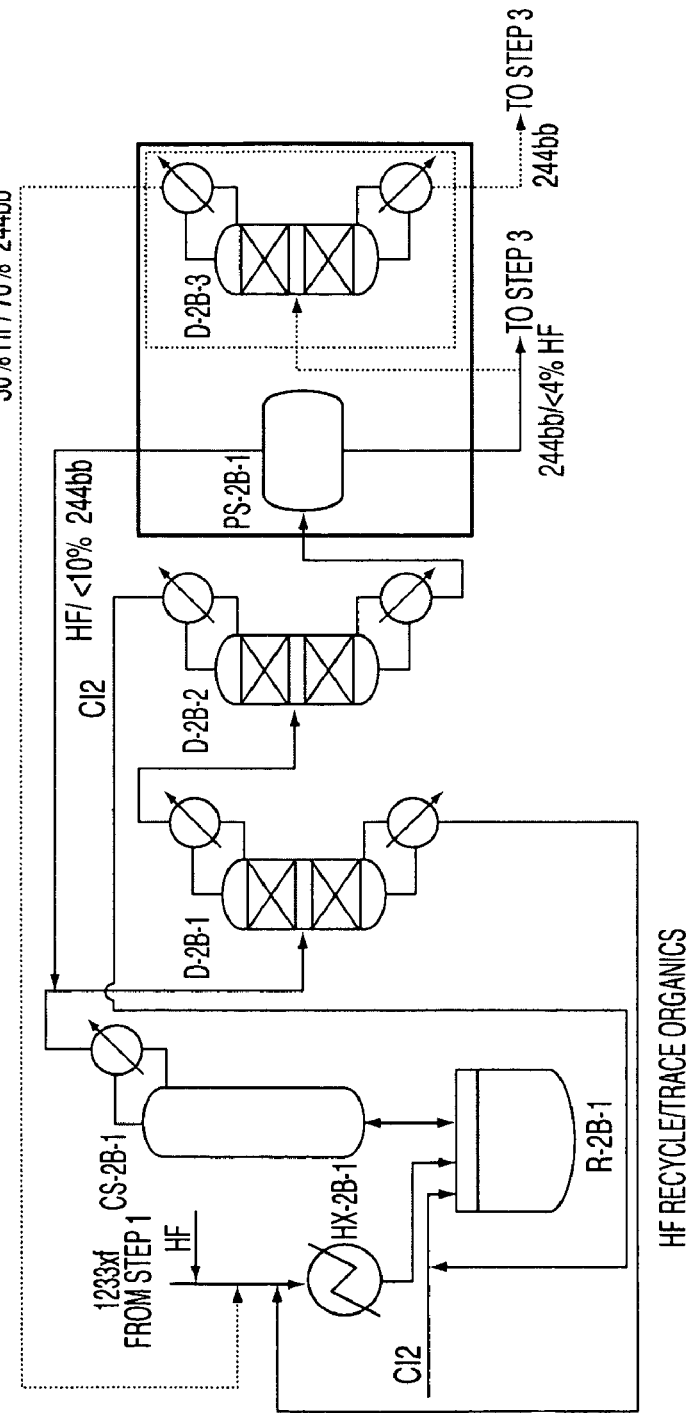
FIG. 5 is a flow diagram showing a second preferred embodiment of a second step of an integrated 3-step process for producing HFO-1234yf starting from 1,1,2,3-tetrachloropropene or 1,1,1,2,3-pentachloropropane.

Referring to FIG. 5, shown is another preferred embodiment of operations 4 through 6. Here, the HCFO-1233xf containing stream from Step 1, Options A, B, or C and excess HF are simultaneously fed to a vaporizer HX-2B-1 and then into a liquid phase reactor R-2B-1. R-2B-1 is a TFE or PFA-lined liquid phase reactor, run at 70-120° C. and 50-120 psig. The catalyst in R-2B-1 is $SbCl_5$ or other Lewis acid catalyst. A catalyst stripper column CS-2B-1 is connected to the reactor, R-2B-1, and serves the purpose of knocking down and returning entrained catalyst, some HF, and some unreacted HCFO-1233xf back to the reactor for further reaction. $Cl_2$ may also be fed to the reactor to keep the catalyst active. It may be fed continuously or batchwise as needed. The stream exiting the top of catalyst stripper CS-2B-1 consisting mainly of HCFC-244bb and HF (plus small amounts of unreacted HCFO-1233xf and $Cl_2$ may also be present)) is fed to a recycle column D-2B-1 where a stream consisting of mainly HF (trace organic) exits the bottom of the recycle column and is recycled back to the Step 2 reactor R-2B-1 via vaporizer HX-2B-1. A stream consisting of mainly HCFC-244bb and HF (plus small amounts of unreacted HCFO-1233xf and $Cl_2$ may also be present) exits the top of the recycle column and is then fed to a $Cl_2$ recovery distillation column, D-2B-2. The stream exiting the top of the recycle column is fed into the $Cl_2$ recovery column and $Cl_2$ is taken overhead and recycled back to the Step 2 reactor, R-2B-1. The $Cl_2$ recovery column bottom stream consisting of mainly HCFC-244bb and HF (plus small amount of unreacted HCFO-1233xf) is then fed into an HF recovery system. The HF recovery system starts with the HCFC-244bb/HF stream being fed into phase separation system PS-2B-1. Here the stream is cooled to −40-0° C. The HF rich top layer (<10% HCFC-244bb) is recycled back to the recycle column D-2B-1. The organic rich bottom layer containing mainly HCFC-244bb (<4% HF+small amount of HCFO-1233xf) is sent forward to Step 3. Optionally, before being sent forward to Step 3, the stream is fed to a distillation column D-2B-3. A stream consisting of mainly HCFC-244bb/HF azeotrope (plus small amount of HCFO-1233xf) exits the top of the column and is recycled back to the Step 2 reactor, R-2B-1, via a vaporizer HX-2B-1.

Figure 6:
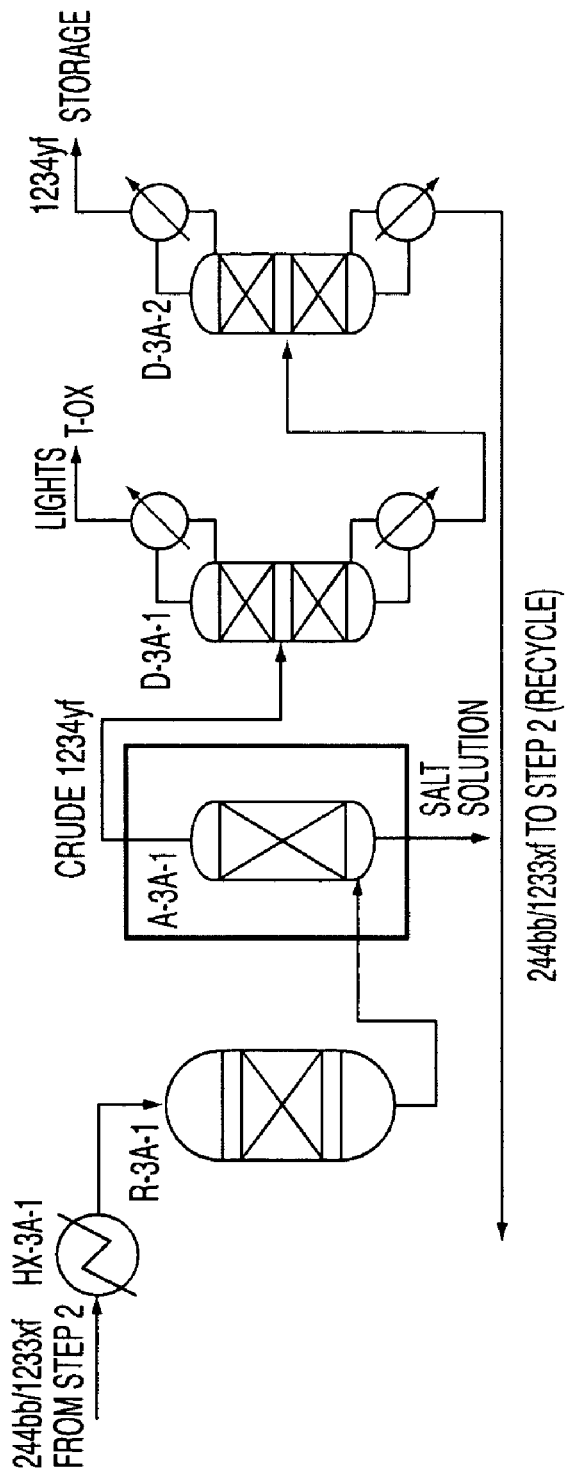
FIG. 6 is a flow diagram showing a first preferred embodiment of a third step of an integrated 3-step process for producing HFO-1234yf starting from 1,1,2,3-tetrachloropropene or 1,1,1,2,3-pentachloropropane.

Referring to FIG. 6, shown is a preferred embodiment of operations 7 through 8. Here, the HCFC-244bb-containing stream from Step 2, Options A or B, are fed to a vaporizer HX-3A-1 and then into a vapor phase reactor R-3A-1. The reaction temperature is about 350-550° C. and the reaction pressure is about 0-150 psig. The following catalysts have been shown to have high selectivity for producing HFO-1234yf in the range of temperatures mentioned above and can be used in R-3A-1: activated carbon, stainless steel (e.g. SS 316), austenitic nickel-based alloys (e.g. Inconel 625), nickel, fluorinated 10% CsCl/MgO, and 10% CsCl/MgF$_2$. The reactor effluent consisting of unreacted HCFC-244bb, HCFO-1233xf, HFO-1234yf, HCl (plus HF and/or Cl$_2$ if certain Step 2 options were employed) then enters acid absorption system A-3A-1 where the gaseous stream contacts a water or a caustic solution (and bisulfite to destroy Cl$_2$ if present) to remove HCl (and HF if present) and is subsequently dried with a desiccant. The gas exiting the top of the acid absorber is fed to a "lights" distillation column D-3A-1. Non-condesables and by-products having lower boiling points than HFO-1234yf exit the top of the "lights" column and are fed to a thermal-oxidizer and eliminated/destroyed. The bottoms from the "lights" column are fed to a HFO-1234yf product column D-3A-2. Product grade HFO-1234yf exits the top of the column to product storage. The product column bottoms consist mainly of unreacted HCFC-244bb and HCFO-1233xf and are recycled back to Step 2 reactor R-2A-1 or R-2B-1 depending on what option that is being employed.

Figure 7:
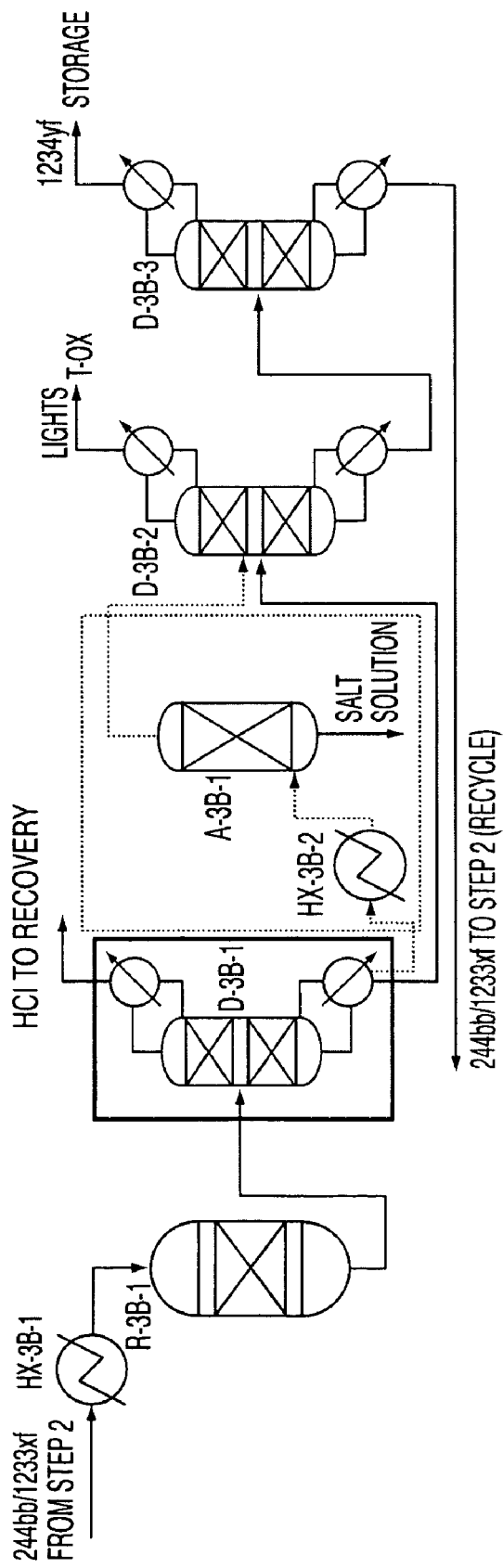
FIG. 7 is a flow diagram showing a second preferred embodiment of a third step of an integrated 3-step process for producing HFO-1234yf starting from 1,1,2,3-tetrachloropropene or 1,1,1,2,3-pentachloropropane.

Referring to FIG. 7, shown is another preferred embodiment of operations 7 through 8. Here, the HCFC-244bb containing stream from Step 2, Options A or B, are fed to a vaporizer HX-3A-1 and then into a vapor phase reactor R-3B-1. The reaction temperature is about 350-550° C. and the reaction pressure is about 0-150 psig. The following catalysts have been shown to have high selectivity for producing HFO-1234yf in the range of temperatures mentioned above and can be used in R-3B-1: activated carbon, stainless steel (e.g. SS 316), austenitic nickel-based alloys (e.g. Inconel 625), nickel, fluorinated 10% CsCl$_2$/MgO, and 10% CsCl$_2$/MgF$_2$. The reactor effluent consisting of unreacted HCFC-244bb, HCFO-1233xf, HFO-1234yf, HCl (plus HF and/or Cl$_2$ if certain Step 2 options were employed) enters HCl column D-3B-1. A stream consisting of mainly HCl by-product exits the top of the HCl column and is fed to an HCl recovery system. The recovered HCl by-product can be sold for profit. The HCl column bottoms consisting mainly of unreacted HCFC-244bb, HCFO-1233xf, and HFO-1234yf (plus HF and/or Cl$_2$ if certain Step 2 options were employed) are then fed to a "lights" distillation column D-3B-2. By-products having lower boiling points than HFO-1234yf exit the top of the "lights" column and are fed to a thermal-oxidizer and eliminated/destroyed. The bottoms from the "lights" column are fed to a HFO-1234yf product column D-3B-3. Product grade HFO-1234yf exits the top of the column to product storage. The product column bottoms consist mainly of unreacted HCFC-244bb and HCFO-1233xf and are recycled back to Step 2 reactor R-2A-1 or R-2B-1 depending on what option that is being employed.

Optionally, if HF and/or Cl$_2$ are present in the HCl column, D-3B-1, they will exit from the bottom of the column. The bottom stream is then vaporized by HX-3B-2 and fed to acid absorption system A-3B-1 where the gaseous stream contacts a water or a caustic solution (and bisulfite to destroy Cl$_2$ if present) to remove HF (and HCl if present) and is subsequently dried with a desiccant. The gas exiting the top of the acid absorber is fed to the "lights" column D-3B-2.

The invention is further described in terms of the following, non-limiting examples.

EXAMPLES

Example 1

This example illustrates Step 1 of the continuous vapor phase fluorination reaction of 1,1,2,3-tetrachloropropene (TCP)+3HF→2-chloro-3,3,3-trifluoropropene (HCFO-1233xf)+3HCl. The fluorination catalyst for the experiment was fluorinated Cr$_2$O$_3$.

A continuous vapor phase fluorination reaction system consisting of N$_2$, HF, and organic feed systems, feed vaporizer, superheater, 4 inch ID Monel reactor, acid scrubber, drier, and product collection system was used to study the reaction. The reactor was loaded with 9415.2 grams of pre-treated Cr$_2$O$_3$ catalyst which equates to about 6.5 liters of catalyst. The reactor was then heated to a reaction temperature of about 235° C. with a N$_2$ purge going over the catalyst after the reactor had been installed in a constant temperature sand bath. The reactor was at about 3 psig of pressure. HF feed was introduced to the reactor (via the vaporizer and superheater) as a co-feed with the N$_2$ for 15 minutes when the N$_2$ flow was stopped. The HF flow rate was adjusted to 1.4 lb/hr and then 1,1,2,3-tetrachloropropene (TCP) feed was started to the reactor (via the vaporizer and superheater). The feed rate of TCP was kept steady at about 0.8 lb/hr and HF feed was kept steady at 1.4 lb/hr for about a 15 to 1 mole ratio of HF to TCP. Once the reaction started the catalyst bed temperature rose to a range of 250-260° C. The contact time at 250-260° C., 3 psig and the above feed rates was calculated to be about 16 seconds. The average composition of the material that was collected over 500 hours of on-stream time was about 97.2 GC area % HCFO-1233xf, 1.6 GC area % HCFC-244bb, 0.6 GC area % HFO-1234yf/HFC-245cb, 0.1 GC area % HCFO-1223xd, and 0.08 GC area % HCFO-1231. After 500 hours an under-fluorinated intermediate, 2,3-dichloro-3,3-difluoro-propene (HCFO-1232xf) started to appear as the selectivity to HCFO-1233xf decreased when the catalyst started losing activity. When the selectivity to HCFO-1233xf decreased to about 83% and the selectivity to underfluorinated intermediate HCFO-1232xf increased to about 15% after 650 hours of on-stream time, the reaction was stopped due to loss of catalyst activity. The conversion of TCP remained at >99% throughout the run.

Example 2

The fluorinated Cr$_2$O$_3$ catalyst deactivated after 650 hours of on-stream time as described in Example 1 was regenerated by the following procedure.

The reactor was heated to 300° C. while flowing N$_2$ at the rate of 5000 cc/min. After reactor temperatures were stabilized, synthetic air was introduced. Air flow was started with a rate that gave 0.5% $O_2$. Gradually, with 0.25% $O_2$ increments, air flow was increased to achieve $O_2$ concentration of 2.0%. Then reactor hot-spot was brought to 360° C. And then air flow rate was gradually, with 0.5-1.0% increments, increased to achieve $O_2$ concentration of 5.0%. Careful adjustments of reactor heater temperature were needed to avoid overheating reactor above 380° C.

The reactor temperature was maintained at a 360-375° C. catalyst bed hot spot temperature while flowing 5% $O_2/N_2$ until the hot spot reached the top of the catalyst bed. Then, without changing reactor heater temperature, $O_2$ flow was maintained until reactor temperature approached that of reactor heater set point. Then, reactor was purged with $N_2$ for 5 hours to remove residual oxygen and moisture. That completed the regeneration of the catalyst and reactor was brought to 200° C. to prepare it for the re-fluorination with HF.

The TCP+3HF→HCFO-1233xf+3HCl reaction was restarted at the same operating conditions described in Example 1. The selectivity of HCFO-1233xf increased to 98.5% after regeneration and intermediate HCFO-1232xf was not detected in the reaction products. The conversion of TCP was 100%.

Example 3

This example illustrates the Step 1 continuous vapor phase fluorination reaction of 1,1,1,2,3-pentachloropropane (HCC-240db)+3HF→2-chloro-3,3,3-trifluoropropene (HCFO-1233xf)+4HCl. The fluorination catalyst for the experiment was fluorinated $Cr_2O_3$.

The same continuous vapor phase fluorination reaction system as described in Example 1 was used for Example 3. The HCC-240db+3HF→HCFO-1233xf+4HCl reaction was run at a 15:1 mole ratio HF to HCC-240db, contact time of 15 seconds, and a reaction temperature of 255° C. GC analysis of the reactor effluent showed 100% conversion of HCC-240db and 98.3% selectivity of HCFO-1233xf on a molar basis. The details of Example 3 are presented in Table 1.

TABLE 1

Exp# 71 HCC-240db + 3HF ----> HCFO-1233xf + 4 HCl

| Component | HFO-1234yf/HFC-245cb | HCFC-244bb | HCFO-1233xf | * HCC-240db | others |
|---|---|---|---|---|---|
| Selectivity | 0.5 | 0.6 | 98.3 | 100.0 | 0.6 |

Fluorinated $Cr_2O_3$ catalyst, 15:1 mole ratio HF to HCC-240db, contact time 15 seconds, Reaction Temperature = 255° C.
* Conversion Example 4

This example illustrates Step 2 of the continuous liquid phase fluorination reaction of 2-chloro-3,3,3-trifluoropropene (HCFO-1233xf)+HF→2-chloro-1,1,1,2-tetrafluoropropane (HCFC-244bb). The fluorination catalyst for the experiment was $SbCl_5$.

About 5618 grams of $SbCl_5$ were contained in a Teflon™-lined liquid phase reactor equipped with a 2-inch ID (inside diameter) packed column and a condenser. The reactor was 2.75-inch ID×36-inch L (length). Initially, a greater than 5:1 mole ratio of HF was added to the reactor to fluorinate the catalyst. A greater than 3:1 mole ratio of $Cl_2$ was then added to the reactor to ensure that the catalyst was brought back to a pentavalent state. The reactor was heated to about 85° C.-87° C. HF feed was started first. When an additional 1.5 lbs of HF had been added the 2-chloro-3,3,3-trifluoropropene feed was started. The purity of the 2-chloro-3,3,3-trifluoropropene feed stock was about 97.3 GC (gas chromatograph) area %. The experiment ran continuously for about 162 hours. For this run, chlorine was fed batchwise about every 4 hours throughout the run to keep the catalyst active.

Conversion was immediately above 98%, and remained that way throughout the rest of the run. The average feed rates of HF and HCFO-1233xf were 0.91 and 0.88 lb/hr respectively. The chlorine additions amounted to about 3.0% by weight of the average organic feed rate. About 123 pounds of acid-free 2-chloro-1,1,1,2-tetrafluoropropane crude were collected.

The reactor temperature range for the experiments was 78° C.-86° C. and the pressure range was 70 psig-105 psig. The reaction was monitored by sampling the reactor effluent stream periodically. The samples were analyzed on a gas chromatograph. The average conversion of 2-chloro-3,3,3-trifluoropropene (HCFO-1233xf) of about 98% and the following average product selectivity: HCFC-244bb=90%, HCFO-1223xd=1% and HFC-245cb=8%.

Example 5

This example illustrates the recovery of anhydrous HF from a mixture of HF and HCFC-244bb according to certain preferred embodiments of the present invention.

A mixture consisting of about 75 wt. % HCFC-244bb and about 25 wt. % HF is vaporized and fed to the bottom of a packed column at a feed rate of about 2.9 lbs per hour for about 4 hours. A stream of about 80 wt. % sulfuric acid (80/20$H_2SO_4/H_2O$) with about 2% HF dissolved therein is fed continuously to the top of the same packed column at a feed rate of about 5.6 lbs per hour during the same time frame. A gaseous stream exiting the top of the column comprises HCFC-244bb with less than 1.0 wt. % HF therein. The concentration of HF in the sulfuric acid in the column bottoms increases from 2.0 wt. % to about 15 wt. %.

The column bottoms containing sulfuric acid and about 15 wt. % HF are collected and charged into a 2 gallon teflon vessel. The mixture is heated to about 140° C. to vaporize and flash off HF product, which is collected. The collected HF product contains about 6000 ppm water and 500 ppm sulfur.

The HF collected from flash distillation is distilled in a distillation column and anhydrous HF is recovered. The recovered anhydrous HF contains less than 50 ppm of sulfur impurities and less than 100 ppm water.

Example 6

This example demonstrates the optional HF recovery distillation of Step 1, Option B after the recovery of the majority of the HF by phase separation. The distillation column feed is a mixture of HF, HCFO-1233xf, and HCFC-244bb.

After phase separation, 37.4 pounds of a mixture containing 3 weight percent HF, 43.1 weight percent HCFC-244bb and 53.9 weight percent HCFO-1233xf was charged into a distillation column. The distillation column consisted of a 10 gallon reboiler, 2 inch ID by 10 foot propack column, and a shell and tube condenser. The column had about 30 theoretical plates. The distillation column was equipped with temperature, pressure, and differential pressure transmitters. The distillation was run at a pressure of about 37.7-39.7 psia. The distillate was sampled, titrated for HF concentration determination, and analyzed by GC at regular intervals. Titration showed an HF concentration in the range of 25-33 wt % (using titration with 0.1 N KOH). The organic concentrations based on GC area % were about 17-21 GC area % HCFC-244bb and about 79-83 GC area % HCFO-1233xf. At 37.7 psia the column overhead temperature was about 23° C. for this composition. When the HF was depleted, as confirmed by titration, the column overhead temperature was about 40° C. at 23 psig. 8.0 lbs of HF containing distillate was collected into a DIT and 29.4 lbs of HF free HCFO-1233xf/HCFC-244bb mixture was drained from the reboiler.

Example 7

This example demonstrates the recycle column of Step 2, Options A and B.

A reactor effluent mixture from a reaction Step 2 experiment was charged into a distillation column. The distillation column consisted of a 10 gallon reboiler, 2 inch ID by 10 foot propack column, and a shell and tube condenser. The column had about 30 theoretical plates. The distillation column was equipped with temperature, pressure, and differential pressure transmitters. The distillation column feed mixture was about 71.5 wt % HF and 28.5 wt % organic. The organic was mostly a mixture of HCFO-1233xf and HCFC-244bb, but contained some light and heavy impurities and some HCFO-1232xf intermediate. The distillation was run at a pressure of about 100 psig. The distillate was sampled, titrated for HF concentration determination, and analyzed by GC at regular intervals. Titration showed an HF concentration in the range of 20-30 wt % (using titration with 0.1 N KOH). In total 38 lbs of distillate was collected that contained about 20-30 wt % HF. The balance was organic having an average GC analysis of 54.5% HCFO-1233xf, 44.5% HCFC-244bb, and 1% light impurities with only ppm levels of higher boiling impurities. The reboiler bottoms were drained to a separate 100 lb cylinder with a Ceodeux dual valve assembly and dip tube. 62 lbs of mainly HF were recovered. Some intermediate HCFO-1232xf and high boiling impurities were observed. The recovered HF (reboiler bottoms) was used to demonstrate recycle in a subsequent Step 2 reaction and worked satisfactorily.

Example 8

This example demonstrates the HF recovery by phase separation of Step 2, Option B, of a HCFC-244bb/HCFO-1233xf/HF mixture.

The separation of organic and HF layers was tested in the temperature range from +10° C. to −30° C. The highest concentration of HF in the organic layer was detected at +10° C. (2.23±0.30 wt. %), the lowest concentration of HF in the organic layer was detected at −30° C. (0.76±0.09 wt. %). The concentration of HF in the HF layer was about 90±5 wt. %. GC analysis of Organic and HF layers indicated that there is no difference in the organic composition between organic and HF layer.

The phase-separation of the mixture containing HCFC-244bb, HCFO-1233xf, and HF was performed in the temperature range of −30° C. to +10° C. A 500 ml SS sample cylinder was used for the study. The temperature of the cylinder was controlled with ethanol circulating through the coil wrapped around the cylinder. A thermocouple was attached to the outside wall of the cylinder (between cooling coil and the cylinder wall) and positioned in the middle of the cylinder to measure the temperature. The cylinder was also equipped with sampling valves at the bottom and the top of the cylinder. To the cylinder were charged 98.7 g of anhydrous HF and 233 g of a 93.0 GC area % HCFC-244bb/5.0 GC area % HCFO-1233xf mixture. The weight ratio of HF to Organic was 29.8:70.2. The cylinder was padded with nitrogen to 12 psig at −30° C. to allow sampling. Samples were taken from the bottom of the cylinder into Tedlar gas sample bags that contained 5 grams of distilled water for the purpose of absorbing HF. The first sample was taken two hours after the cylinder reached the desired temperature. After this, the contents of the cylinder were mixed and a second sample was taken five minutes after mixing. HF concentration was determined by titration with 0.1 N KOH of the aqueous phase of the sample bags. HF concentration in samples taken after 2 hours at given temperature is presented in Table 2. HF concentration in samples taken 5 minutes after mixing contents of the cylinder at given temperature is presented in Table 3.

HF concentration in the HF layer was analyzed after organic layer was removed from the system. KOH titration showed that concentration of HF in the acid layer was about 90±5%. The distribution of organics in HF layer was the same as in the Organics layer.

TABLE 2

HF concentration in the samples of the bottom (organic) phase taken after equilibrating the contents of the phase-separator for 2 hours at given temperature.

| Temperature (° C.) | HF concentration in bottom (organic) phase (wt. %) | Standard deviation |
| --- | --- | --- |
| −30 | 0.76 | 0.09 |
| −20 | 0.89 | 0.13 |
| −10 | 1.25 | 0.11 |
| 0 | 1.63 | 0.15 |
| 10 | 2.23 | 0.30 |

TABLE 3

HF concentration in the samples of the bottom (organic) phase taken 5 minutes after mixing the contents of the phase-separator.

| Temperature (° C.) | HF concentration in bottom (organic) phase (wt. %) | Standard deviation |
| --- | --- | --- |
| −30 | 0.84 | 0.08 |
| −20 | 1.05 | 0.26 |
| −10 | 1.37 | 0.07 |
| 0 | 1.71 | 0.22 |
| 10 | 2.61 | 0.35 |

Figure 8:
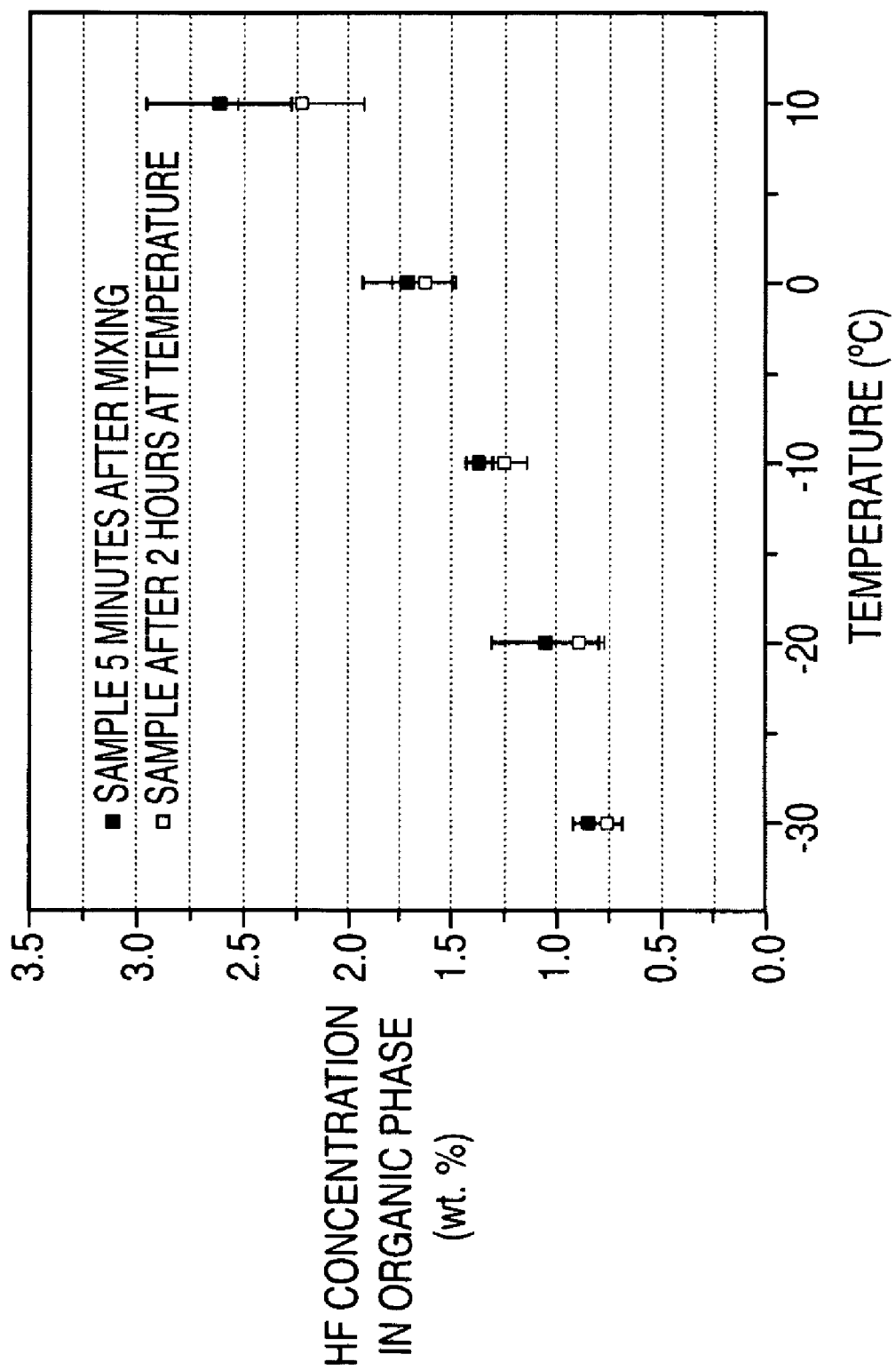
FIG. 8 is a plot of HF as a function of temperature for HF recovery by phase separation of Step 2, Option B, of a HCFC-244bb/HCFO-1233xf/HF mixture.

The HF concentration is shown graphically FIG. 8.

Example 9

This example illustrates the Step 3 continuous vapor phase dehydrochlorination reaction of 2-chloro-1,1,1,2-tetrafluoropropane (HCFC-244bb)→2,3,3,3-tetrafluoropropene (HFO-1234yf)+HCl. The dehydrochlorination catalyst for the experiment was 10 wt % CsCl/90 wt % $MgF_2$.

Conversion of HCFC-244bb into HFO-1234yf was performed using Monel reactor (ID 2 inches, length 32 inches) equipped with a Monel preheater (ID 1 inch, length 32 inches) which was filled with Nickel mesh to enhance heat transfer. The reactor was filled with 2.0 liters of pelletized 10 wt % CsCl/90 wt % $MgF_2$ dehydrochlorination catalyst. Nickel mesh was placed at the top and at the bottom of reactor to support the catalyst. A multi-point thermocouple was inserted at the center of the reactor. The catalyst was pretreated in dry $N_2$ flow for 6 hours at the temperature of 480° C. Then the feed with the composition 95 GC % HCFC-244bb/3.1 GC %

HCFO-1233xf/0.35 GC % HFC-245cb was introduced into the reactor at the rate of 1.0 lb/hr. The feed was vaporized prior to entering the reactor preheater. The feed rate was maintained constant at 1.0 lbs/hr and both temperature and pressure were varied. Temperature gradient throughout the reactor never exceeded 3-5° C. The productivity of the catalyst was estimated at 3-6 lbs/hr/ft³. The highest productivity was observed at 470° C. and 45 psig, and the lowest productivity was observed at 480° C. and 3 psig. The reaction products were fed into a caustic scrubber to remove HCl byproduct. Then the product stream was passed through a column filled with desiccant to remove residual moisture. An oil-less compressor was used to feed crude product into the distillation column that was maintained at 30-45 psig pressure. Distillation was performed in a continuous mode and the take-off rate was equal to the rate of production of HFO-1234yf in the reactor. The purity of distilled HFO-1234yf was 99.9+GC area %. GC analysis of the distillate showed the presence of ppm levels of light impurities The bottoms of the distillation column were discharged and recycled into the dehydrochlorination reactor.

480° C. at 3 psig—HCFC-244bb conversion ~30%, Selectivity to HFO-1234yf ~97%

480° C. at 20 psig—HCFC-244bb conversion ~47%, Selectivity to HFO-1234yf ~96%

470° C. at 20 psig—HCFC-244bb conversion ~36%, Selectivity to HFO-1234yf ~97%

470° C. at 45 psig—HCFC-244bb conversion ~53%, Selectivity to HFO-1234yf ~96%

460° C. at 45 psig—HCFC-244bb conversion ~38%, Selectivity to HFO-1234yf ~98%

Figure 9:
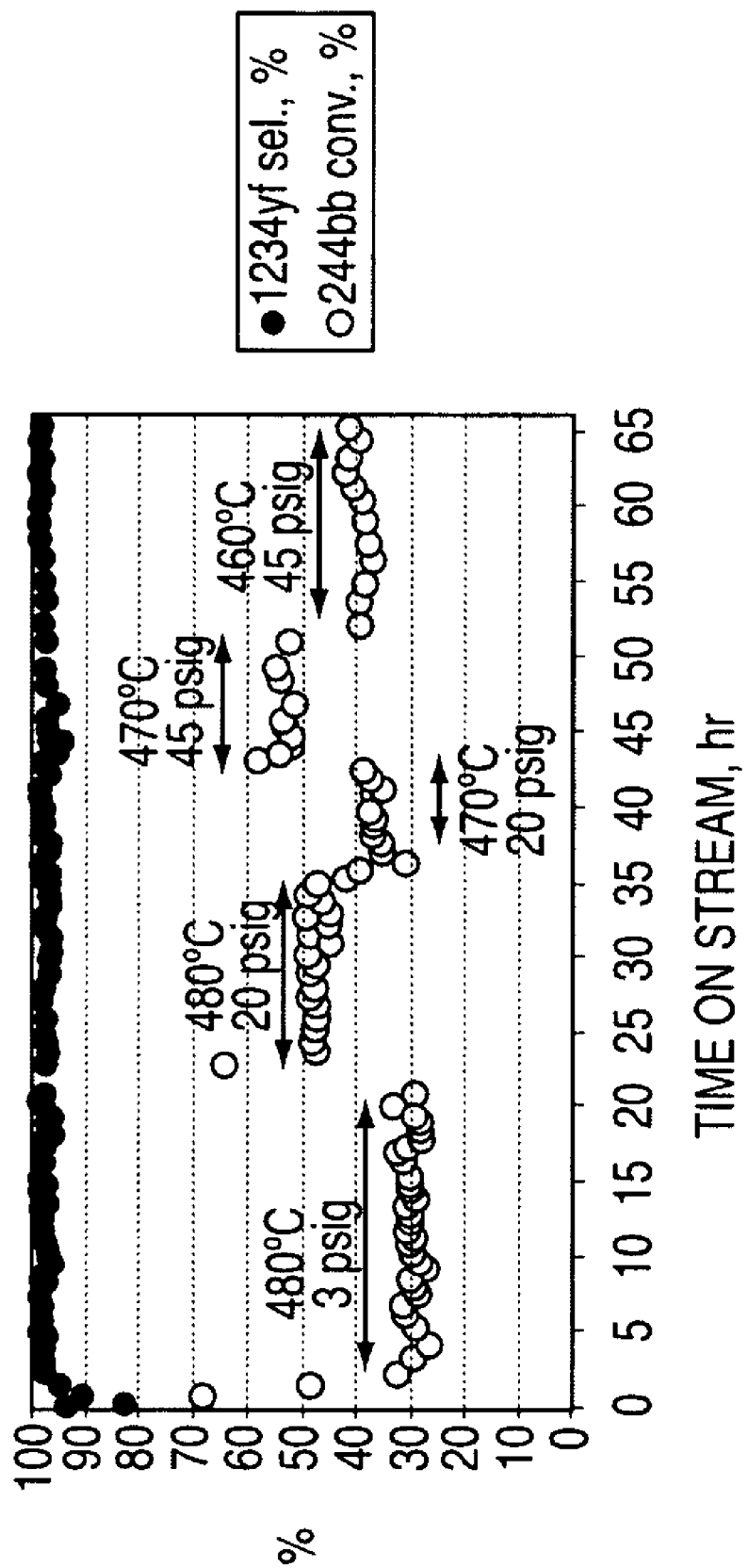
FIG. 9 is a plot of the selectivity of HFO-1234yf and the percent conversion of HCFC-244bb according to certain embodiments of the invention as a function of time at various temperatures and pressures.

Reaction Conditions Feed=about 95 GC % HCFC-244bb; about 3.1 GC % HCFO-1233xf; and about 0.35 GC % HFC-245cb; 2.0 liters of 10 wt % CsCl/90 wt % MgF₂ catalyst; 1.0 lb/hr feed rate. The reaction data is represented graphically in FIG. 9.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

The invention claimed is:

1. A method for preparing 2,3,3,3-tetrafluoroprop-1-ene comprising:
   a. providing a starting composition comprising at least one compound having a structure selected from Formulae I, II and III:

$$CX_2=CCl-CH_2X \quad \text{(Formula I)}$$

$$CX_3-CCl=CH_2 \quad \text{(Formula II)}$$

$$CX_3-CHCl-CH_2X \quad \text{(Formula III)}$$

wherein X is independently selected from F, Cl, Br, and I, provided that at least one X is not fluorine;
   b. contacting said starting composition with a first fluorinating agent to produce a first intermediate composition comprising 2-chloro-3,3,3-trifluoropropene and a first chlorine-containing byproduct;
   c. contacting said first intermediate composition with a second fluorinating agent to produce a second intermediate composition comprising 2-chloro-1,1,1,2-tetrafluoropropane; and
   d. dehydrochlorinating at least a portion of said 2-chloro-1,1,1,2-tetrafluoropropane to produce a reaction product comprising 2,3,3,3-tetrafluoroprop-1-ene and a second chlorine-containing byproduct.

2. The method of claim 1 further comprising the step of removing at least a portion of said first chlorine-containing byproduct from said first intermediate composition subsequent to, and/or concurrently with, said contacting step (b).

3. The method of claim 2 further comprising the step of removing at least a portion of said second chlorine-containing byproduct from said product subsequent to, and/or concurrently with, said step (d).

4. The method of claim 1 wherein at least one X is chlorine.

5. The method of claim 4 wherein a majority of X is chlorine.

6. The method of claim 5 wherein said compound according to Formula I is 1,1,2,3-tetrachloropropene.

7. The method of claim 5 wherein said compound according to Formula II is 2,3,3,3-tetrachloropropene.

8. The method of claim 5 wherein said compound according to Formula III is 1,1,1,2,3-pentachloropropane.

9. The method of claim 1 wherein said first and second chlorine-containing byproducts comprise hydrogen chloride.

10. The method of claim 1 wherein said contacting step (b) comprises a vapor-phase catalytic fluorination of said compound having a structure according to Formulae I, II, or III.

11. The method of claim 10 wherein said first fluorinating agent is hydrogen fluoride.

12. The method of claim 11 further comprising the step of separating at least a portion of said hydrogen fluoride from said 2-chloro-3,3,3-trifluoropropene subsequent to, or concurrently with, step (b) and prior to step (c).

13. The method of claim 12 wherein said first fluorinating agent comprises at least a portion of said hydrogen fluoride separated from said 2-chloro-3,3,3-trifluoropropene.

14. The method of claim 1 wherein said contacting step (c) comprises a liquid-phase fluorination of said 2-chloro-3,3,3-trifluoropropene in the presence of a catalyst.

15. The method of claim 14 wherein said second fluorinating agent is hydrogen fluoride.

16. The method of claim 15 wherein further comprising the step of separating at least a portion of said hydrogen fluoride from said 2-chloro-1,1,1,2-tetrafluoropropane subsequent to, or concurrently with, step (c) and prior to step (d).

17. The method of claim 16 wherein said second fluorinating agent comprises at least a portion of said hydrogen fluoride separated from said 2-chloro-1,1,1,2-tetrafluoropropane.

18. The method of claim 1 wherein said dehydrochlorination is conducted in the vapor phase and in the presence of a catalyst.

19. The method of claim 1 wherein said 2,3,3,3-tetrafluoroprop-1-ene is separated from said reaction product via at least one distillation operation.

* * * * *